US006231882B1

(12) United States Patent
Modi

(10) Patent No.: US 6,231,882 B1
(45) Date of Patent: *May 15, 2001

(54) MIXED MICELLAR DELIVERY SYSTEM AND METHOD OF PREPARATION

(75) Inventor: Pankaj Modi, Ancaster (CA)

(73) Assignee: Generex Pharmaceuticals Inc., Toronto (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/216,733

(22) Filed: Dec. 21, 1998

Related U.S. Application Data

(63) Continuation-in-part of application No. 09/021,114, filed on Feb. 10, 1998.
(51) Int. Cl.[7] .............................. A61F 13/00; A61F 9/02; A61K 9/127; A61K 38/00; A61L 9/04
(52) U.S. Cl. ........................ 424/434; 424/400; 424/435; 424/436; 424/450; 424/45; 514/2; 514/3; 514/946; 514/947
(58) Field of Search .............................. 424/45, 400, 434, 424/435, 436, 450; 514/946, 947, 2, 3

(56) References Cited

U.S. PATENT DOCUMENTS 6,017,545 * 1/2000 Modi ................................. 424/400

* cited by examiner

Primary Examiner—Thurman K. Page
Assistant Examiner—Todd D. Ware
(74) Attorney, Agent, or Firm—Debra Z. Anderson; Eckert Seamans Cherin & Mellott, LLC

(57) ABSTRACT

A mixed micellar pharmaceutical formulation includes a micellar proteinic pharmaceutical agent, an alkali metal C8 to C22 alkyl sulphate, alkali metal salicylate, a pharmaceutically acceptable edetate and at least one absorption enhancing compounds. The absorption enhancing compounds are selected from the group consisting of lecithin, hyaluronic acid, pharmaceutically acceptable salts of hyaluronic acid, octylphenoxypolyethoxyethanol, glycolic acid, lactic acid, chamomile extract, cucumber extract, oleic acid, linolenic acid, borage oil, evening of primrose oil, trihydroxy oxo cholanylglycine, glycerin, polyglycerin, lysine, polylysine, triolein and mixtures thereof. The amount of each absorption enhancing compound is present in a concentration of from 1 to 10 wt./wt. % of the total formulation, and the total concentration of absorption enhancing compounds are less than 50 wt./wt. % of the formulation.

30 Claims, No Drawings

MIXED MICELLAR DELIVERY SYSTEM AND METHOD OF PREPARATION

This is a continuation-in-part of application Ser. No. 09/021,114 filed Feb. 10, 1998.

FIELD OF THE INVENTION

The present invention relate to an improved delivery system for the administration of large-molecule pharmaceuticals, e.g. peptidic drugs, vaccines and hormones. In particular it relates to pharmaceuticals which may be administered through the oral and nasal membranes.

BACKGROUND TO THE INVENTION

In spite of significant efforts in academic and commercial laboratories, major breakthroughs in oral peptide and protein formulation have not been achieved. Relatively little progress has been made in reaching the target of safe and effective oral formulations for peptides and proteins. The major barriers to developing oral formulations for proteins and peptides include poor intrinsic permeability, lumenal and cellular enzymatic degradation, rapid clearance, and chemical stability in the gastrointestinal (GI) tract. Pharmaceutical approaches to address these barriers, which have been successful with traditional small, organic drug molecules, have not readily translated into effective peptide and protein formulations. Although the challenges are significant, the potential therapeutic benefits remain high especially in the field of diabetes treatment using insulin.

Scientists have explored various administration routes other than the injection for proteins and peptides. These routes include oral, intranasal, rectal, vaginal cavities for the effective delivery of large molecules. Out of the above four mentioned routes oral and nasal cavities have been of greatest interest to scientists. Both the oral and nasal membranes offer advantages over other routes of administration. For example, drugs administered through these membranes have a rapid onset of action, provide therapeutic plasma levels, avoid first pass effect of hepatic metabolism, and avoid exposure of the drug to hostile GI environment. Additional advantages include easy access to the membrane sites so that the drug can be applied, localized and removed easily. Further, there is a good potential for prolonged delivery of large molecules through these membranes.

The oral routes have received far more attention than has the other routes. The sublingual mucosa includes the membrane of ventral surface of the tongue and the floor of the mouth whereas the buccal mucosa constitutes the lining of the cheek. The sublingual mucosa is relatively permeable thus giving rapid absorption and acceptable bioavailability of many drugs. Further, the sublingual mucosa is convenient, acceptable and easily accessible. This route has been investigated clinically for the delivery of a substantial number of drugs.

The ability of molecules to permeate through the oral mucosa appears to be related to molecular size, lipid solubility and peptide protein ionization. Small molecules, less than 1000 daltons appear to cross mucosa rapidly. As molecular size increases, the permeability decreases rapidly. Lipid soluble compounds are more permeable than non-lipid soluble molecules. Maximum absorption occurs when molecules are un-ionized or neutral in electrical charges. Therefore charged molecules present the biggest challenges to absorption through the oral mucosae.

Most proteinic drug molecules are extremely large molecules with molecular weight exceeding 6000 daltons. These large molecules have very poor lipid solubility and are practically impermeable. Substances that facilitate the absorption or transport of large molecules (>2000 daltons) across biological membranes are known as the enhancers, (Lee et al., Critical Reviews in Therapeutic drug Carrier Systems, 8, 91, 1991; Lee et al., Critical Reviews in Therapeutic drug Carrier Systems, 8, 115, 1991, 1992). Enhancers may be characterized as chelators, bile salts, fatty acids, synthetic hydrophillic and hydrophobic compounds, and biodegradable polymeric compounds.

Various mechanisms of action of enhancers have been proposed. These mechanisms of action, at least for protein and peptidic drugs include (1) reducing viscosity and/or elasticity of mucous layer, (2) facilitating transcellular transport by increasing the fluidity of the lipid bilayer of membranes, and (3) increasing the thermodynamic activity of drugs (Critical Rev, 117–125, 1991, 1992).

Many enhancers have been tested so far and some have found to be effective in facilitating mucosal administration of large molecule drugs. However, hardly any penetration enhancing products have reached the market place. Reasons for this include lack of a satisfactory safety profile respecting irritation, lowering of the barrier function, and impairment of the mucocilliary clearance protective mechanism. The main factor to be considered in the use of enhancers especially related to bile salts, and some protein solubilizing agents is extremely bitter and unpleasant taste. This makes their use almost impossible for human consumption on a daily basis. Several approaches were utilized to improve the taste of the bile salts based delivery systems, but none one of them are commercially acceptable for human consumption to date. Among the approaches utilized includes patch for buccal mucosa, bilayer tablets, controlled release tablets, use of protease inhibitors, buccally administered film patch devices, and various polymer matrices.

The basic problem associated with the above technologies is the use of large quantities of bile acids and their salts to promote the transport of the large molecules through membranes in the form of localized delivery system using patches or tablets. In spite of using protease inhibitors and polymer coatings the technologies failed to deliver proteinic drugs in the required therapeutic concentrations. Further, the problem is compounded because of the localized site effect of the patch which resulted in severe tissue damage in the mouth. Most attempts were made to deliver large molecules via the oral, nasal, rectal, and vaginal routes using single bile acids or enhancing agents in combination with protease inhibitors and biodegradable polymeric materials. However, it is extremely difficult to achieve therapeutic levels of proteinic drugs using these formulations. As single enhancing agents fails to loosen tight cellular junctions in the oral, nasal, rectal and vaginal cavities for a required period of time to allow passage of large molecules through the mucosal membranes without further degradation. This problem makes it impractical to use the above mentioned systems for a commercial purpose.

In order to overcome the above mentioned problem of the bitter taste, irritation and the penetration of large molecules through the sublingual, buccal and GI tract mucosal lining, a system has now been designed where protein drug was encapsulated in mixed micelles made up of combination of enhancers, e.g. yolk proteins (lecithins). This system allows opening of the paracellular junctions (tight junctions) in oral as well as in GI tract by gI motility movement with high degree of protease activity preserved and protecting molecules from premature degradation in the hostile acidic and proteolytic GI environment.

It is believed that the mixed micelles encapsulate molecules with high degree of efficiency (>90w encapsulation). These mixed micelles are extremely small in the size (1 nm to 10 nm), and are smaller than the pores of the membranes in the oral cavity or the GI tract. It is therefore believed that the extremely small size of mixed micelles helps encapsulated molecules penetrate efficiently through the mucosal membranes of the oral cavity.

The absorption of proteins and peptides is believed to be enhanced by the diffusion of large molecules entrapped in the mixed micellar form through the aqueous pores and the cell structure perturbation of the tight paracellular junctions.

The amount of physiologically peptide or protein in the compositions of this invention is typically a quantity that provides an effective amount of the drug to produce the physiological activity (therapeutic plasma level) for which peptide or protein is being administered. In consideration of the fact that the bioavailability of any active substance can never be 100%, that is to say the administered dose of the active drug is not completely absorbed, it is preferable to incorporate slightly larger amount than the desired dosage. Where the dosage form is a spray (aerosol) or the like which is repeatedly dispensed from the same container, it is recommendably so arranged that the unit dose will be slightly greater than the desired dose. It should be understood that dosage should vary with species of warm blood animals such as man, domestic animals, and their body weights. Although the composition of this invention is prepared as the microfine droplets (1 to 10 nm or less) by the virtue of its preparation methods used and suitable combinations of enhancer compound characteristics. The utilization of atomizer or aerosol spray devices (metered dose inhalers or nebulizers) may be useful to further a sufficient reduction of particle size for effective inhalation from the nasal or oral cavity so the drug may successfully absorbed or reach to the specific site.

The therapeutic composition of the present invention can be stored at room temperature or at cold temperature. Storage of proteinic drugs is preferable at the cold temperature to prevent the degradation of the drugs and to extend their shelf life. While the mixed micellar therapeutic composition of the invention is applied to the mucosal membranes, the sites of administration may the same as those used for the usual mucosal therapeutic preparation. Generally, oral, transdermal and nasal are the favourite sites of the administration but the composition can be applied to the rectal and vaginal mucosa. According to the physiologically active peptide or protein used, the dosage form and the site of administration, a specific administration method can be selected.

As used herein, the term "edetate" is used herein to refer to pharmaceutically acceptable salts of ethylenediaminetetraacetic acid.

It has also been found that improvements in penetration and absorption of mixed micellar formulations can be achieved by mixing the mixed micellar formulation with propellants such as tetrafluoroethane, heptafluoroethane, dimethylfluoropropane, tetrafluoropropane, butane, isobutane, dimethyl ether and other non-CFC and CFC propellants. Preferably they are delivered through metered dose spray devices. Metered dose inhalers are known and are a popular pulmonary drug delivery form for some drugs. The present formulation, including the propellant is intended to improve the quality of absorption, stability and performance of many formulations. The compositions have been selected to give enhancement in the penetration through pores, and facilitate absorption of the drugs to reach therapeutic levels in the plasma. The present formulation may be absorbed buccally, by ensuring that the person does not inhale the formulation as it is sprayed. One of the other benefits of using an atomizer or inhaler is that the potential for contamination is minimized because the devices are self contained.

SUMMARY OF THE INVENTION

Accordingly the present invention provides a mixed micellar pharmaceutical formulation, having a pH of between 6.0 and 7.0 comprising a proteinic pharmaceutical agent in micellar form, water, an alkali metal lauryl sulphate in a concentration of from 1 to 10 wt./wt. % of the total formulation, a pharmaceutically acceptable edetate in a concentration of from 1 to 10 wt./wt. % of the total formulation, at least one alkali metal salicylate in a concentration of from 1 to 10 wt./wt. % of the total formulation, and at least one micelle forming compound selected from the group consisting of lecithin, hyaluronic acid, pharmaceutically acceptable salts of hyaluronic acid, octylphenoxypolyethoxyethanol, glycolic acid, lactic acid, chamomile extract, cucumber extract, oleic acid, linolenic acid, borage oil, evening of primrose oil, trihydroxy oxo cholanylglycine, glycerin, polyglycerin, lysine, polylysine, triolein and mixtures thereof, wherein the amount of each absorption enhancing compound is present in a concentration of from 1 to 10 wt./wt. % of the total formulation, and the total concentration of absorption enhancing compounds are less than 50 wt./wt. % of the formulation.

In an embodiment, the alkali metal lauryl sulphate, the edetate and the alkali metal salicylate are each in a concentration of from 2 to 5 wt./wt. % of the total formulation.

In one embodiment, the edetate is an alkali metal edetate. Preferably the alkali metal edetate is be selected from the group consisting of disodium edetate, dipotassium edetate, and combinations thereof.

In another embodiment, the alkali metal lauryl sulphate is sodium lauryl sulphate.

In a further embodiment, the alkali metal salicylate is sodium salicylate.

In another embodiment, the lecithin is selected from the group consisting of saturated phospholipid, e.g. Phospholipon-H (trade mark) saturated phospholipid, unsaturated phospholipid, e.g. Phospholipon-G (trade mark) unsaturated phospholipid, phosphatidylcholine, phosphatidyl serine, sphingomyelin, phosphatidylethanolamine, cephalin, and lysolecithin.

In one embodiment, one of the absorption enhancing compounds is selected from the group consisting of hyaluronic acid, pharmaceutically acceptable salts of hyaluronic acid and mixtures thereof, the concentration such micelle forming compound being from about 1 to about 5 wt./wt. %.

In another embodiment, suitable for delivery through nasal passages, mixed micellar pharmaceutical formulation is suitably diluted to avoid irritation of the nasal passages.

Another aspect of the present invention provides a mixed micellar pharmaceutical formulation, comprising a pharmaceutical agent in micellar form, water, an alkali metal C8 to C22 alkyl sulphate in a concentration of from 1 to 10 wt./wt. % of the total formulation, a pharmaceutically acceptable edetate in a concentration of from 1 to 10 wt./wt. % of the total formulation, at least one alkali metal salicylate in a concentration of from 1 to 10 wt./wt. % of the total formulation, and at least one micelle forming compound selected from the group consisting of lecithin, hyaluronic acid, pharmaceutically acceptable salts of hyaluronic acid, octylphenoxypolyethoxyethanol, glycolic acid, lactic acid, chamomile extract, cucumber extract, oleic acid, linolenic acid, borage oil, evening of primrose oil, menthol, trihydroxy oxo cholanylglycine and pharmaceutically acceptable salts thereof, glycerin, polyglycerin, lysine, polylysine, polidocanol alkyl ethers and analogues thereof, triolein and mixtures thereof, wherein the amount of each absorption enhancing compound is present in a concentration of from 1 to 10 wt./wt. % of the total formulation, and the total concentration of absorption enhancing compounds are less than 50 wt./wt. % of the formulation.

Yet another aspect of the present invention provides that the mixed micellar aerosol pharmaceutical formulation additionally comprises i) a phenol selected from the group consisting of phenol and methyl phenol in a concentration of from 1 to 10 wt./wt. % of the total formulation, and i) a propellant selected from the group consisting of C1–C2 dialkyl ether, butanes, fluorocarbon propellant, hydrogen-containing fluorocarbon propellant, chlorofluorocarbon propellant, hydrogen-containing chlorofluorocarbon propellant, and mixtures thereof.

In one embodiment, the alkali metal C8 to C22 alkyl sulphate is in a concentration of from 2 to 5 wt./wt. % of the total formulation.

In another embodiment, the alkali metal C8 to C22 alkyl sulphate is sodium lauryl sulphate.

In another embodiment, the lecithin is saturated or unsaturated, preferably selected from the group consisting of phosphatidylcholine, phosphatidyl serine, sphingomyelin, phosphatidylethanolamine, cephalin, and lysolecithin.

In yet another embodiment, one of the micelle forming compounds is selected from the group consisting of hyaluronic acid, pharmaceutically acceptable salts of hyaluronic acid, polidocanol alkyl ethers, trihydroxy oxo cholanyl glycine, polyoxyethylene ethers and mixtures thereof, the concentration such absorption enhancing compound being from about 1 to about 5 wt./wt. %.

Preferably, the ratio of pharmaceutical agent, e.g. insulin, to propellant is from 5:95 to 25:75.

In another embodiment, the propellant is selected from the group consisting of tetrafluoroethane, tetrafluoropropane, dimethylfluoropropane, heptafluoropropane, dimethyl ether, n-butane and isobutane.

In yet another embodiment, the mixed micellar pharmaceutical formulation is contained in an aerosol dispenser.

For insulin-containing and some other compositions, the composition may also contains at least one inorganic salt which opens channels in the gastrointestinal tract and may provide additional stimulation to release insulin. Non-limiting examples of inorganic salts are sodium, potassium, calcium and zinc salts, especially sodium chloride, potassium chloride, calcium chloride, zinc chloride and sodium bicarbonate.

It will be recognized by those skilled in the art that for many pharmaceutical compositions it is usual to add at least one antioxidant to prevent degradation and oxidation of the pharmaceutically active ingredients. It will also be understood by those skilled in the art that colorants, flavouring agents and non-therapeutic amounts of other compounds may be included in the formulation. Typical flavouring agents are menthol and sorbitol.

In one embodiment the antioxidant is selected from the group consisting of tocopherol, deteroxime mesylate, methyl paraben, ethyl paraben and ascorbic acid and mixtures thereof. A preferred antioxidant is tocopherol.

In a preferred embodiment at least one protease inhibitor is added to the formulation to inhibit degradation of the pharmaceutical agent by the action of proteolytic enzymes of the known protease inhibitors, most are effective at concentrations of from 1 to 3 wt./wt. % of the formulation.

Non-limiting examples of effective protease inhibitors are bacitracin, soyabean trypsin, aprotinin and bacitracin derivatives, e.g. bacitracin methylene disalicylate. Bacitracin is the most effective of those named when used in concentrations of from 1.5 to 2 wt./wt. %. Soyabean trypsin and aprotinin two may be used in concentrations of about 1 to 2 wt./wt. % of the formulation.

The formulation suitable for delivery through oral mucosal membranes may be in chewable form, in which case it will be necessary to add ingredients suitable for such form. Such ingredients include guar gum, powdered acacia, carrageenin, beeswax and xanthan gum.

The pharmaceutical agent may be selected from a wide variety of macromolecular agents, depending on the disorder being treated, generally with molecular weights greater than about 1000 and especially between about 1000 and 2000000. Preferred pharmaceutical agents are selected from the group consisting of insulin, heparin, low molecular weight heparin, hirulog, hirugen, huridine, interferons, interleukins, cytokins, mono and polyclonal antibodies, immunoglobins, chemotherapeutic agents, vaccines, glycoproteins, bacterial toxoids, hormones, calcitonins, insulin like growth factors (IGF), glucagon like peptides (GLP-1), large molecule antibiotics, protein based thrombolytic compounds, platelet inhibitors, DNA, RNA, gene therapeutics and antisense oligonucleotides, and small molecule drugs, e.g. opioids, narcotics, analgesics, NSAIDS, steroids, hypnotics, pain killers, morphine and the like.

The present invention also provides a process for making a pharmaceutical composition suitable for delivery through transdermal membranes comprising:

a) preparing a proteinic pharmaceutical agent composition in micellar form in an aqueous medium which has an alkali metal salicylate in a concentration of from 1 to 10 wt./wt. % of the aqueous micellar pharmaceutical agent composition, an alkali metal lauryl sulphate in a concentration of from 1 to 10 wt./wt. % of the aqueous micellar pharmaceutical agent composition and a pharmaceutically acceptable edetate in a concentration of from 1 to 10 wt./wt. % of the aqueous micellar pharmaceutical agent composition;

b) slowly adding the micellar proteinic pharmaceutical agent composition to at least one of the absorption enhancing compounds selected from the group consisting of lecithin, hyaluronic acid, pharmaceutically acceptable salts of hyaluronic acid, octylphenoxypolyethoxyethanol, glycolic acid, lactic acid, chamomile extract, cucumber extract, oleic acid, linolenic acid, borage oil, evening of primrose oil, trihydroxy oxo cholanylglycine, glycerin, polyglycerin, lysine, polylysine, triolein and mixtures thereof, while mixing vigorously, to form a mixed micellar composition;

wherein the amount of the absorption enhancing compounds are each present in a concentration of from 1 to 10 wt./wt. % of the total formulation, and the total concentration of alkali metal salicylate, alkali metal lauryl sulphate, edetate and absorption enhancing compounds is less than 50 wt./wt. % of the formulation.

In one embodiment, the process provides an additional step of adding, while continuing vigorous mixing, at least one absorption enhancing compound different from that added in step b), selected from the group consisting of lecithin, hyaluronic acid, pharmaceutically acceptable salts of hyaluronic acid, octylphenoxypolyethoxyethanol, glycolic acid, lactic acid, chamomile extract, cucumber extract, oleic acid, linolenic acid, borage oil, evening of primrose oil, trihydroxy oxo cholanylglycine, glycerin, polyglycerin, lysine, polylysine, triolein and mixtures thereof.

In one embodiment the alkali metal lauryl sulphate is sodium lauryl sulphate.

In another embodiment the alkali metal salicylate is sodium salicylate.

In a further embodiment the alkali metal edetate may be selected from the group consisting of disodium edetate and dipotassium edetate.

In yet another embodiment, the formulation has a combinations selected from the group consisting of sodium hyaluronate and unsaturated phospholipid, ii) Phospholipon-H and glycolic acid, and iii) sodium hyaluronate and lecithin.

The present invention also provides a process for making a pharmaceutical composition suitable for delivery by means of an aerosol comprising:

a) preparing a pharmaceutical agent composition in micellar form in an aqueous medium which has an alkali metal C8 to C22 alkyl sulphate in a concentration of from 1 to 10 wt./wt. % of the aqueous micellar pharmaceutical agent composition, a pharmaceutically acceptable edetate in a concentration of from 1 to 10 wt./wt. % of the aqueous micellar pharmaceutical agent composition, at least one alkali metal salicylate in a concentration of from 1 to 10 wt./wt. % of the aqueous micellar pharmaceutical agent composition;

b) slowly adding the micellar proteinic pharmaceutical agent composition to at least one of the absorption enhancing compounds selected from the group consisting of lecithin, hyaluronic acid, pharmaceutically acceptable salts of hyaluronic acid, octylphenoxypolyethoxyethanol, glycolic acid, lactic acid, chamomile extract, cucumber extract, oleic acid, linolenic acid, borage oil, evening of primrose oil, menthol, trihydroxy oxo cholanylglycine and pharmaceutically acceptable salts thereof, glycerin, polyglycerin, lysine, polylysine, polidocanol alkyl ethers and analogues thereof, triolein and mixtures thereof, while mixing vigorously, to form a mixed micellar composition; and optionally c) an additional step of adding, while continuing vigorous mixing, at least one micelle forming compound different from that added in step b), selected from the group consisting of lecithin, hyaluronic acid, pharmaceutically acceptable salts of hyaluronic acid, glycolic acid, lactic acid, chamomile extract, cucumber extract, oleic acid, linoleic acid, linolenic acid, monoolein, borage oil, evening of primrose oil, glycerin, polyglycerin, lysine, polylysine, triolein, polyoxyethylene ethers and analogues thereof, polidocanol alkyl ethers and analogues thereof, and mixtures thereof;

d) mixing the mixed micellar composition resulting from steps a) to c) with a phenol selected from the group consisting of phenol, m-cresol and mixtures thereof; and subsequently e) placing the formulation into an aerosol dispenser and charging the dispenser a propellant;

wherein each of the absorption enhancing compounds are present in a concentration of from 1 to 10 wt./wt. % of the total formulation, and the total concentration of alkali metal salicylate, alkali metal C8 to C22 alkyl sulphate, edetate and absorption enhancing compounds is less than 50 wt./wt. % of the formulation.

The vigorous mixing may be accomplished using high speed stirrers. The vigorous mixing may be accomplished by using high speed stirrers, e.g. magnetic stirrers or propellor stirrers, or by sonication.

In one embodiment, the mixed micellar formulation is formed by sonication of the aqueous micellar pharmaceutical agent composition in the presence of lecithin.

DETAILED DESCRIPTION OF PREFERRED EMBODIMENTS

The present invention provides an improved method for delivery of macromolecular (high molecular weight) pharmaceutical agents, particularly through the membranes in the nose, mouth, vagina or rectum. The preferred delivery is through oral and nasal cavities. The pharmaceutical agents cover a wide spectrum of agents, including proteins, peptides, hormones, vaccines and drugs. The molecular weights of the macromolecular pharmaceutical agents are preferably above 1000, especially between 1000 and 2000000.

For example, hormones which may be administered with the present invention include thyroids, androgens, estrogens, prostaglandins, somatotropins, gonadotropins, erythropoetin, interferons, interleukins, steroids and cytokins. Vaccines which may be administered with the present invention include bacterial and viral vaccines such as vaccines for hepatitis, influenza, tuberculosis, canary pox, chicken pox, measles, mumps, rubella, pneumonia, BCG, HIV and AIDS. Bacterial toxoids which may be administered using the present invention include diphtheria, tetanus, pseudonomas and mycobactrium tuberculosis. Examples of specific cardiovascular or thrombolytic agents include heparin, hirugen, hirulos and hirudin. Large molecules usefully administered with the present invention include monoclonal antibodies, polyclonal antibodies and immunoglobins.

As will be understood, the concentration of the pharmaceutical agent is an amount sufficient to be effective in treating or preventing a disorder or to regulate a physiological condition in an animal or human. The concentration or amount of pharmaceutical agent administered will depend on the parameters determined for the agent and the method of administration, e.g. oral, nasal. For example, nasal formulations tend to require much lower concentrations of some ingredients in order to avoid irritation or burning of the nasal passages. It is sometimes desirable to dilute an oral formulation up to 10–100 times in order to provide a suitable nasal formulation.

The mixed micellar formulation is prepared by first preparing a first micellar composition which contains the pharmaceutically active agents, alkali metal C8 to C22 alkyl sulphate, edetate and alkali metal salicylate. For those compositions intended for administration through the nasal, oral, vaginal or rectal cavities, the first micellar composition is then added to at least one of the absorption enhancing compounds to form a mixed micellar composition. At least one other absorption enhancing compound may also be added subsequently. Preferably the first absorption enhancing compound is lecithin.

When making the aerosol formulation, the phenol and/or m-cresol and/or isotonic agent are then added. The formulation is then put into an aerosol dispenser and the dispenser charged with the propellant.

The preferred propellants are hydrogen-containing chlorofluorocarbons, hydrogen-containing fluorocarbons, dimethyl ether and diethyl ether. Even more preferred is hydrofluoroalkane (HFA) 134a (1,1,1,2 tetrafluoroethane).

Although the present invention has such wide applicability, the invention is described hereinafter with particular reference to insulin and its analogues, which are used for the treatment of diabetes.

As indicated hereinbefore, the compositions of the present invention require that the pharmaceutical formulation be in mixed micellar form.

In the case of insulin, which is intended for administration through nasal or oral cavities, the first micellar solution may be made by adding a buffer solution to powdered insulin, and then stirring until the powder is dissolved and a clear solution is obtained. A typical buffer solution is an aqueous solution of sodium salicylate and sodium lauryl sulphate and disodium edetate. Typical concentration of sodium salicylate and sodium lauryl sulphate in the aqueous solution are about 3 to 20 wt./wt. % of each compound in the solution. Typically, insulin is present in the micellar solution in an amount which will give a concentration of about 2 to 4 wt./wt. % of the final formulation. Typically the concentration may be about 10 wt./wt. % of the first micellar composition.

The micellar solution is then added slowly to the first absorption enhancing compound, e.g. lecithin while mixing vigorously, e.g. sonicating, to form a mixed micelle liposomal solution. At least one other absorption enhancing compounds selected from the group consisting of lecithin, hyaluronic acid, pharmaceutically acceptable salts of hyaluronic acid, octylphenoxypolyethoxyethanol, glycolic acid, lactic acid, chamomile extract, cucumber extract, oleic acid, linolenic acid, borage oil, evening of primrose oil, trihydroxy oxo cholanylglycine, glycerin, polyglycerin, lysine, polylysine, triolein is then added. The mixing may be done with a high speed mixer or sonicator to ensure uniform micelle particle size distribution within the formulation.

Each of the absorption enhancing compounds, when present, is in a concentration of from 1 to 10 wt./wt. % of the total formulation.

Preferred salts of hyaluronic acid are alkali metal hyaluronates, alkaline earth hyaluronates and aluminium hyaluronate. The preferred salt is sodium hyaluronate. The preferred concentration of hyaluronic acid or pharmaceutically acceptable salts of hyaluronic acid is from 1 to 5 wt./wt. % of the total formulation. An even more preferred range is from 1.5 to 3.5 wt./wt. % of the total formulation.

Other ingredients may be added to the mixed micellar solution. For example, flavouring agents, antioxidants, salts, protease inhibitors or other pharmaceutically acceptable compound may be added.

In general the size of the micelle particles in the solution is about 1 to 10 nm, and preferably from 1 to 5 nm. Such a size distribution ensures effective absorption of the formulation, and therefore the pharmaceutical agent, through the membranes, for example the membranes in the oral and nasal cavities.

The specific concentrations of the essential ingredients can be determined by relatively straightforward experimentation. For absorption through the nasal and oral cavities, it is often desirable to increase, e.g. double or triple, the dosage which is normally required through injection of administration through the gastrointestinal tract.

As will be understood, the amount of each component of the formulation will vary depending on the pharmaceutical agent and the site of application. Preferred formulations oral or nasal application have the following combinations: i) sodium lauryl sulphate, sodium salicylate, disodium edetate, Phospholipon-H and sodium hyaluronate; ii) sodium lauryl sulphate, sodium salicylate, disodium edetate, lecithin and sodium hyaluronate; iii) sodium lauryl sulphate, sodium salicylate, disodium edetate, sodium hyaluronate and evening of primrose oil; iv) sodium lauryl sulphate, sodium salicylate, disodium edetate, Phospholipon-H and bacitracin; v) sodium lauryl sulphate, sodium salicylate, disodium edetate, Phospholipon-H, sodium hyaluronate and bacitracin; and vi) sodium lauryl sulphate, sodium salicylate, disodium edetate, sodium hyaluronate, oleic acid and gamma linoleic acid.

For aerosol formulations, the addition of a mixture of phenol and m-cresol is preferred. Such an aerosol formulation may then be charged to an aerosol dispenser and then charged with a propellant, preferably a non-CFC propellant.

The therapeutic compositions of the present invention may be stored at room temperature or at cold temperature. Storage of proteinic drugs is preferable at a cold temperature to prevent degradation of the drugs and to extend their shelf life.

As indicated hereinbefore, generally, oral and nasal are the favourite sites of the administration but the composition can be applied to the rectal and vaginal mucosa. According to the physiologically active peptide or protein used, the dosage form and the site of administration a specific administration method can be selected.

The composition of this invention is generally prepared as microfine mixed micellar particles (1 to 10 nm or less) by the virtue of its preparation methods used and suitable combinations of absorption enhancer characteristics.

For oral and nasal application, sprays are preferable, but also drops, chewable tablets, chewable gum and other suitable forms may be used. Utilization of atomizer or aerosol spray devices (metered dose inhalers or nebulizers) can be used to further reduce the particle size for effective inhalation from the nasal or oral cavity so the drug may successfully reach to the specific site and be absorbed. It is also possible to utilize a drug delivery system such that an enteric coating is applied to the gelatin capsule to cause the micelles to be released only in the duodenum or in the proximity of the large intestine and not in the stomach.

The invention is illustrated by reference to the following examples.

EXAMPLE 1

A first experiment was conducted to provide data for comparative purposes. This example does not fall within the scope of the present invention.

A solution was prepared using 0.5 g sodium lauryl sulphate, 0.5 g sodium salicylate and 0.25 g disodium edetate dissolved in 10 mL of water. To this solution 40 mg (1000 units) of insulin was added and dissolved completely while stirring, to give about 100 units/mL insulin solution.

In one set of tests, five healthy non-diabetic human volunteers were tested with insulin, by injection. In another set of tests the volunteers were tested with insulin, taken orally. The volunteers fasted from midnight prior to the test, with no food being taken during the 4 hour study.

On the first day, the volunteers received 10 units insulin by injection (regular fast acting insulin, available from Eli Lilly). On the second day, the volunteers received 100 units (1 mL volume per drop, approximately 20 drops) of the above-prepared oral insulin (10 times the injection dose). In both tests, blood glucose levels were monitored every 15 minutes by Bayer's Glucometer Elite.

The average results for the five volunteers, of the first day's trial (sub-cutaneous injection with 10 units) were as follows:

TABLE I

| Time*: | 0 | 15 | 30 | 60 | 75 | 90 | 120 | 150 | 180 |
|---|---|---|---|---|---|---|---|---|---|
| Avg: | 5.8 | 5.8 | 5.4 | 5.0 | 4.6 | 4.3 | 3.8 | 3.6 | 3.4 |
| Time*: | 210 | 240 | | | | | | | |
| Avg: | 4.2 | 4.5 | | | | | | | |

*time in minutes

The results for each of the five volunteers, of the second day's trial (oral drops with 100 units) were as follows:

TABLE II

| Time*: | 0 | 15 | 30 | 60 | 75 | 90 | 120 | 150 | 180 | 210 | 240 |
|---|---|---|---|---|---|---|---|---|---|---|---|
| Subject Nos: | | | | | | | | | | | |
| 1 | 6.2 | 5.8 | 5.2 | 5.0 | 4.9 | 5.0 | 5.0 | 4.8 | 4.7 | 5.5 | 6.0 |
| 2 | 5.8 | 5.4 | 5.0 | 4.7 | 4.9 | 4.3 | 5.0 | 5.5 | 5.2 | 5.8 | 6.1 |
| 3 | 4.8 | 4.6 | 4.3 | 4.3 | 4.4 | 4.6 | 4.8 | 4.7 | 5.2 | 5.5 | 5.1 |
| 4 | 6.6 | 6.1 | 5.8 | 5.5 | 5.1 | 4.9 | 5.0 | 5.0 | 5.9 | 6.2 | 6.8 |
| 5 | 6.0 | 5.8 | 5.7 | 5.5 | 5.1 | 4.8 | 4.7 | 4.9 | 5.0 | 5.9 | 6.7 |

*time in minutes

These tests indicate that compared to the injection method, oral insulin gives a faster onset of action and lowers blood glucose levels without creating hypoglycaemic condition. Due to the hepatic glucose production, there was a rebound effect. This is believed to be due to the incomplete absorption of insulin.

EXAMPLE 2

Another experiment, not within the scope of the present invention, was performed for comparative purposes.

Oral insulin (100 units) was formulated in (Phospholipon-H, 10 mg) without any sodium lauryl sulphate, sodium salicylate, edetate or absorption enhancers, to evaluate its efficacy of blood glucose lowering in a fasted state, for healthy volunteers.

Volunteers were asked to fast overnight and not have any breakfast prior to dosing. Volunteers were asked to take this oral insulin formulation in their mouth and swallow it. Blood glucose levels were monitored every 15 minutes using Bayer's glucometer Elite for 3 hours, and the average results for 5 volunteers are shown in Table III.

TABLE III

| Time*: | 0 | 15 | 30 | 45 | 60 | 75 | 90 | 120 | 150 | 180 |
|---|---|---|---|---|---|---|---|---|---|---|
| Avg: | 5.6 | 5.8 | 5.8 | 5.7 | 5.7 | 5.8 | 5.7 | 5.7 | 5.8 | 5.7 |

*time in minutes

This indicates that orally administered insulin with lecithin alone has no effect on blood glucose lowering.

EXAMPLE 3

A further experiment, not within the scope of the present invention, was performed for comparative purposes.

Oral insulin (100 units) was formulated with sodium salicylate and alkali metal edetate (both 5% by wt.) to evaluate its efficacy of blood glucose lowering in fasted state in healthy volunteers.

Volunteers were asked to fast overnight and not have any breakfast prior to dosing. Volunteers were asked to take this oral insulin formulation in their mouth and swallow it. Blood glucose levels were monitored every 15 minutes using Bayer's glucometer Elite for 3 hours and the average results for 5 volunteers are shown in Table IV.

TABLE IV

| Time*: | 0 | 15 | 30 | 45 | 60 | 75 | 90 | 120 | 150 | 180 |
|---|---|---|---|---|---|---|---|---|---|---|
| Avg: | 5.8 | 5.8 | 5.8 | 5.9 | 5.8 | 5.9 | 5.7 | 5.9 | 6.2 | 6.0 |

*time in minutes

This indicates that orally administered insulin with sodium salicylate and alkali metal edetate alone has no effect on blood glucose lowering. In addition, this formulation caused irritation and burning sensation, which lasted for several hours.

EXAMPLE 4

A further experiment, not within the scope of the present invention, was performed for comparative purposes.

Oral insulin (100 units) was formulated using sodium salicylate and alkali metal edetate (both 5% by wt.) with Phospholipon-H (10 mg) and tested on healthy subjects. Blood glucose levels were monitored every 15 minutes using Bayer's glucometer Elite for 3 hours and the results are shown in Table V.

TABLE V

| Time*: | 0 | 15 | 30 | 45 | 60 | 90 | 120 | 180 |
|---|---|---|---|---|---|---|---|---|
| Avg: | 5.3 | 5.3 | 5.3 | 5.4 | 5.6 | 5.7 | 5.7 | 5.8 |

*time in minutes

This indicates that orally administered insulin with sodium salicylate, alkali metal edetate and Phospholipon-H has no effect on blood glucose lowering.

EXAMPLE 5

Another experiment, not within the scope of the present invention, was performed for comparative purposes.

Oral insulin (50 units) was formulated using only alkali metal lauryl sulphate (5% by wt). Blood glucose levels were monitored every 15 minutes using Bayer's glucometer Elite for 3 hours and the average results for four volunteers are shown in Table VI.

TABLE VI

| Time*: | 0 | 15 | 30 | 60 | 90 | 120 | 180 |
|---|---|---|---|---|---|---|---|
| Avg: | 5.8 | 5.6 | 5.4 | 5.3 | 5.4 | 5.4 | 5.6 |

*time in minutes

This data shows that orally administered insulin with only alkali metal lauryl sulphate has little metabolic effect on the blood glucose lowering in healthy subjects. This formulation caused substantial burning sensation and irritation in the subjects and lasted for two days.

EXAMPLE 6

Yet another experiment, within the scope of the present invention, was performed.

Mixed micellar oral insulin (50 units) was formulated using alkali metal lauryl sulphate and sodium salicylate (both 4.4% by wt.) and alkali metal edetate (2.2% by wt) with Phospholipon-H (10 mg) and tested on healthy volunteers.

The method involved mixing the sodium lauryl sulphate, sodium salicylate and alkali metal edetate with water in a beaker with a magnetic stirrer at medium speed until the ingredients were dissolved, to form buffer solution. Insulin powder was placed in a beaker and to this powder was added the buffer solution. The solution was continuously stirred using a magnetic stir bar until all of the insulin powder was dissolved and a clear solution obtained. The micellar solution so formed was stored in clean glass bottles and refrigerated.

Mixed micellar liposomal insulin was then prepared in a glass beaker, in which was placed the Phospholipon-H and a small amount of isopropyl alcohol. The mixture was stirred at a high speed (1000 rpm) for about 10 minutes to ensure complete dissolution of the Phospholipon-H. To this solution was added the micellar insulin solution very slowly, drop wise, using glass dropper, with continuous stirring at a high speed. The solution was stirred continuously for another 30 minutes at a high speed to ensure uniform micellar particle size distribution.

Samples of the mixed micellar solution were taken orally by the volunteers.

Blood glucose levels were monitored every 15 minutes using Bayer's glucometer Elite for 3 hours and the average results for 5 volunteers are shown in Table VII.

TABLE VII

| Time*: | 0 | 15 | 30 | 45 | 60 | 90 | 120 | 150 | 180 |
|---|---|---|---|---|---|---|---|---|---|
| Avg: | 6.5 | 6.1 | 5.5 | 5.3 | 5.3 | 5.4 | 5.5 | 5.5 | 5.5 |

*time in minutes

This data shows that orally administered insulin with alkali metal lauryl sulphate combined with the sodium salicylate and alkali metal edetate with Phospholipon-H has a small metabolic effect on blood glucose levels in healthy volunteers.

EXAMPLE 7

An experiment, within the scope of the present invention, was performed. In this example, the formulation was for oral administration.

Oral insulin (50 units) was formulated using alkali metal lauryl sulphate and sodium salicylate (both 4.46 by wt.) and alkali metal edetate (2.2% by wt.) with Phospholipon-H (10 mg) and sodium hyaluronate (1.1% by wt). This formulation was tested on healthy subjects under fasting condition.

The method involved mixing the sodium lauryl sulphate, sodium salicylate and alkali metal edetate with water in a beaker with a magnetic stirrer at medium speed until the ingredients were dissolved, to form buffer solution. Insulin powder was placed in a beaker and to this powder was added the buffer solution. The solution was continuously stirred using a magnetic stir bar until all of the insulin powder was dissolved and a clear solution obtained. The micellar solution so formed was stored in clean glass bottles and refrigerated.

Mixed micellar liposomal insulin was then prepared in a glass beaker, in which was placed the Phospholipon-H and a small amount of isopropyl alcohol. The mixture was stirred at a high speed (1000 rpm) for about 10 minutes to ensure complete dissolution of the Phospholipon-H. To this solution was added the micellar insulin solution very slowly, drop wise, using glass dropper, with continuous stirring at a high speed. The solution was stirred continuously for another 30 minutes at a high speed to ensure uniform micellar particle size distribution. The hyaluronate and small amounts of menthol and sorbitol were then added, with continuous stirring.

Samples of the mixed micellar solution were taken orally by the volunteers.

Blood glucose levels were monitored every 15 minutes using Bayer's glucometer Elite for 3 hours and the average results for 5 volunteers are shown in Table VIII.

TABLE VIII

| Time*: | 0 | 15 | 30 | 45 | 60 | 90 | 120 | 150 | 180 |
|---|---|---|---|---|---|---|---|---|---|
| Avg: | 6.5 | 5.9 | 5.6 | 5.4 | 4.9 | 5.0 | 4.9 | 5.2 | 5.4 |

*time in minutes

This data shows that orally administered insulin with alkali metal lauryl sulphate, sodium salicylate, alkali metal edetate, Phospholipon-H and sodium hyaluronate has resulted in lowering of blood glucose levels in healthy subjects better than the above mentioned formulations.

EXAMPLE 8

A further experiment, within the scope of the present invention, was performed. In this example, the formulation was for oral administration.

A buffer solution was prepared using 0.5 g sodium lauryl sulphate, 0.5 g sodium salicylate and 0.25 g disodium edetate dissolved in 10 mL of water. The solution was added to insulin and mixed, to form micellar insulin.

Separately, 100 mg of powdered Phosphatidylcholin-H was added to a glass beaker and to this powder was added 10 mL 50% ethanol. The powder was dissolved completely. To this solution 16 mg (400 units) of micellar insulin solution dissolved in 3 mL of the buffer solution to (give 30 units/mL insulin solution) was added slowly with vigorous mixing, to form a mixed micellar solution. To this was added 0.6 mL of sodium hyaluronate and 0.2 ml of 2% menthol solution containing 3% sorbitol.

In one set of tests, ten Type II diabetic human volunteers who took insulin, by injection three times a day, were studied. In another set of tests the volunteers were tested with insulin, taken orally. The volunteers fasted from midnight prior to the test, with no food being taken during the 4 hour study.

On the first day, the volunteers received 10 units insulin by injection (regular fast acting insulin, available from Eli Lilly). On the second day, the volunteers received 30 units (1 mL volume per drop, approximately 20 drops) of the above-prepared oral insulin (3 times the injection dose). In both tests, blood glucose levels were monitored every 15 minutes by Bayer's Glucometer Elite.

The results, showing the average for the ten volunteers, were as shown on the following page:

TABLE IX

Blood glucose levels (mmol/L)

| Time (minutes) | Oral Dose (30 units) | Injection (10 units) |
|---|---|---|
| 0 | 6.4 | 6.8 |
| 15 | 5.8 | 6.9 |
| 30 | 5.4 | 6.1 |
| 45 | 5.3 | 5.8 |
| 60 | 5.3 | 5.8 |
| 75 | 5.2 | 5.8 |
| 90 | 5.2 | 5.4 |
| 105 | 5.2 | 5.4 |
| 120 | 5.1 | 5.2 |
| 135 | 5.1 | 5.1 |
| 150 | 5.2 | 4.9 |
| 165 | 5.3 | 4.9 |
| 180 | 5.3 | 4.8 |
| 195 | 5.4 | 4.8 |
| 210 | 5.4 | 5.2 |
| 225 | 5.6 | 5.2 |
| 240 | 5.6 | 5.4 |

The results show that the oral insulin formulation of the present invention, at a dosage of three times higher than the injected level, is comparable to the injected insulin.

EXAMPLE 9

This example illustrates a method for making a mixed micellar formulation according to the present invention.

In a 250 mL capacity glass beaker was added 5 g sodium lauryl sulphate, 5 g sodium salicylate and 2.5 g edetate. The beaker was placed on the hot plate with a magnetic stirrer. To this dry powder mixture was added 100 mL distilled water and the mixture was stirred, using the magnetic stir bar, at a medium speed until all the powder was dissolved. The buffer solution was stored in a clean glass bottle at room temperature (pH 6.5).

A micellar insulin solution was then prepared in a 50 mL capacity glass beaker, into which was placed 11.54 mg insulin powder. To this powder was added 10 mL of the buffer solution. The solution was continuously stirred using a magnetic stir bar until all of the insulin powder was dissolved and a clear solution obtained. The micellar solution so formed was stored in clean glass bottles and refrigerated.

A 2% menthol solution was then prepared from 100 mg menthol crystals, dissolved in 5 mL ethanol. To this solution was added 5 mg FD & C blue dye. The solution was stirred for 10 minutes and stored in a glass bottle at room temperature.

Mixed micellar liposomal insulin was then prepared in a 50 mL glass beaker, in which was placed 100 mg of phosphatidylcholine (Sigma, type I=EH, hydrogenated). To this powder was added 10 mL of isopropyl alcohol. The mixture was stirred at a high speed (1000 rpm) for about 10 minutes to ensure complete dissolution of the phosphatidylcholine. To this solution was added the micellar insulin solution very slowly, drop wise, using glass dropper, with continuous stirring at a high speed. The solution was stirred continuously for another 30 minutes at a high speed to ensure uniform micellar particle size distribution. To this solution was added 1 mL of the 2% menthol solution and 50 mg sodium hyaluronate. The semi-clear, translucent, light blue colour, liposomal insulin mixed micellar solution (final volume 15 mL) was stored in a clean glass bottle and refrigerated. The solution had a pH of 6.5.

If the phosphatidylcholine powder does not dissolve completely, then heating up to about 45° C. may be required, e.g. using a water bath.

It has been found that if the micellar insulin composition is not added slowly, then the mixed micellar formulation will not be formed and the formulation will be gelatinous and sticky.

EXAMPLE 10

The formulation of Example 9 was tested in a manner similar to that indicated in Example 8 except that the formulation of the present invention was administered nasally.

On the first day, the ten volunteers each received 10 units insulin injection (regular fast acting, Eli Lilly). On the second day, the volunteers received 20 units of the "oral" insulin of Example 9 (2 times the injection dose). The "oral" insulin was administered as drops (0.4 mL volume per drop, approximately 4 large drops in total, i.e. two drops in each nostril).

The results, showing the average for the ten volunteers, were as follows:

TABLE X

Blood glucose levels (mmol/L)

| Time (minutes) | Nasal Dose (20 units) | Injection (10 units) |
|---|---|---|
| 0 | 7.4 | 6.8 |
| 15 | 6.7 | 7.0 |
| 30 | 5.9 | 6.8 |
| 45 | 5.3 | 6.3 |
| 60 | 5.0 | 6.3 |
| 75 | 5.2 | 5.8 |
| 90 | 5.1 | 5.2 |
| 105 | 5.0 | 5.0 |
| 120 | 4.6 | 5.2 |
| 135 | 4.5 | 4.2 |
| 150 | 4.3 | 4.6 |
| 165 | 4.3 | 4.0 |
| 180 | 4.8 | 4.1 |
| 195 | 5.3 | 4.3 |
| 210 | 5.4 | 4.5 |
| 225 | 5.7 | 4.7 |
| 240 | 5.6 | 5.0 |

The results show that the nasal insulin formulation of the present invention, at a dosage of twice the injected level, is comparable to the injected insulin.

EXAMPLE 11

The formula of Example 9 was taken and tests performed to determine the insulin action on meal glucose on healthy volunteers.

Usually, diabetic patients take an insulin injection 30 minutes prior to a meal, because injected insulin takes a long time to take effect. Injected insulin is slowly absorbed into bloodstream within 60 minutes and has metabolic effect on meal glucose levels.

The mixed micellar formulation of Example 9 was tested in healthy volunteers under controlled conditions to determine the oral insulin effect on meal glucose when compared to injected insulin.

In one set of tests, ten healthy non-diabetic human volunteers were tested with insulin, by injection. In another set of tests the volunteers were tested with insulin, taken orally. The volunteers fasted from midnight prior to the tests, with food being taken 30 minutes after dosing. The meals were standard Sastacal 240 mL liquid diet approved by the Diabetic Society, containing 400 calories.

On the first day, the volunteers received 10 units insulin by injection (regular fast acting insulin, available from Eli Lilly). On the second day, the volunteers received 30 units of the above-prepared oral insulin (3 times the injection dose). In both tests, blood glucose levels were monitored every 15 minutes by Bayer's Glucometer Elite. The results are shown on the following page:

TABLE XI

Blood glucose levels (mmol/L)

| Time (minutes) | Oral Dose (30 units) | Injection (10 units) |
|---|---|---|
| 0 | 5.7 | 5.5 |
| 15 | 5.2 | 5.6 |
| 30 | 5.0 | 5.4 |
| 45 | 5.3 | 5.4 |
| 60 | 5.4 | 5.6 |
| 75 | 6.3 | 6.6 |
| 90 | 6.9 | 7.0 |
| 105 | 6.0 | 5.9 |
| 120 | 5.8 | 5.6 |
| 135 | 5.5 | 5.1 |
| 150 | 5.1 | 4.8 |
| 165 | 4.9 | 4.6 |
| 180 | 4.8 | 4.3 |

The results indicate that the oral insulin helps control meal glucose levels in healthy volunteers when compared to injected insulin.

EXAMPLE 12

The mixed micellar formulation of Example 9 was tested in diabetic volunteers under controlled conditions to determine the oral insulin effect on meal glucose when compared to injected insulin.

In one set of tests, ten Type II diabetic human volunteers who took insulin, by injection three times a day, were studied. In another set of tests the volunteers were tested with insulin, taken orally. The volunteers fasted from midnight prior to the tests, with food being taken 30 minutes after dosing. The meals were standard Sastacal 240 mL liquid diet approved by the Diabetic Society, containing 400 calories.

On the first day, the volunteers received 10 units insulin by injection (regular fast acting insulin, available from Eli Lilly). On the second day, the volunteers received 30 units of the above-prepared oral insulin (3 times the injection dose). In both tests, blood glucose levels were monitored every 15 minutes by Bayer's Glucometer Elite.

The average results for the 10 volunteers were as follows:

TABLE XII

Blood glucose levels (mmol/L)

| Time (minutes) | Oral Dose (30 units) | Injection (10 units) |
|---|---|---|
| 0 | 8.8 | 8.7 |
| 15 | 8.1 | 8.8 |
| 30 | 8.0 | 8.9 |
| 45 | 8.4 | 10.1 |
| 60 | 10.2 | 11.8 |
| 75 | 11.8 | 11.8 |

TABLE XII-continued

Blood glucose levels (mmol/L)

| Time (minutes) | Oral Dose (30 units) | Injection (10 units) |
|---|---|---|
| 90 | 12.3 | 12.2 |
| 105 | 10.8 | 11.2 |
| 120 | 9.6 | 10.4 |
| 135 | 8.1 | 8.4 |
| 150 | 6.9 | 7.3 |
| 165 | 6.2 | 6.5 |
| 180 | 4.8 | 4.3 |

The results indicate that oral insulin helps to control meal glucose levels in diabetic patients when compared to injected insulin.

EXAMPLE 13

A chewable gum insulin formulation was prepared by vigorously stirring the liposomal insulin mixed micellar solution of Example 9 while adding guar gum, beeswax, powdered acacia, oleic acid, gamma-linoleic acid and sorbitol. For each 30 units of insulin, the mixture contained 100 mg guar gum, 50 mg beeswax, 50 mg powdered acacia, 100 mg oleic acid, 100 mg gamma-linoleic acid and 1 mL 3% sorbitol in ethanol solution. The mixture was then poured into a flat tray coated with polytetrafluoroethylene until the mixture was about 10 mm deep. The mixture then solidified and after solidification was cut into sticks about 1 cm by 3 cm. Each stick contained about 30 units insulin.

The mixed micellar formulation in chewable stick form was tested in diabetic volunteers under controlled conditions to determine the oral insulin effect on meal glucose when compared to injected insulin.

In one set of tests, five Type II diabetic human volunteers who took insulin, by injection three times a day, were studied. In another set of tests the volunteers were tested with the chewable gum insulin, taken orally. The volunteers fasted from midnight prior to the tests, with food being taken 30 minutes after dosing. The meals were standard Sastacal 240 mL liquid diet approved by the Diabetic Society, containing 400 calories.

On the first day, the volunteers received 10 units insulin by injection (regular fast acting insulin, available from Eli Lilly). On the second day, the volunteers received 30 units of the above-prepared chewable gum oral insulin (3 times the injection dose). In both tests, blood glucose levels were monitored every 15 minutes by Bayer's Glucometer Elite.

The average results for the five volunteers were as follows:

TABLE XIII

Blood glucose levels (mmol/L)

| Time (minutes) | Oral Dose (30 units) | Injection (10 units) |
|---|---|---|
| 0 | 9.1 | 8.8 |
| 15 | 9.3 | 8.2 |
| 30 | 9.3 | 8.0 |
| 45 | 10.2 | 8.4 |
| 60 | 11.2 | 9.2 |
| 75 | 12.1 | 10.3 |
| 90 | 12.9 | 11.8 |
| 105 | 13.2 | 11.6 |

TABLE XIII-continued

Blood glucose levels (mmol/L)

| Time (minutes) | Oral Dose (30 units) | Injection (10 units) |
|---|---|---|
| 120 | 12.8 | 11.0 |
| 135 | 12.2 | 10.2 |
| 150 | 11.6 | 9.6 |
| 165 | 11.0 | 9.5 |
| 180 | 10.6 | 9.1 |
| 195 | 10.0 | 8.7 |
| 210 | 9.5 | 8.2 |
| 225 | 8.8 | 8.0 |
| 240 | 8.2 | 7.5 |

EXAMPLE 14

Another experiment, within the scope of the present invention, was performed. In this example, the formulation was for oral administration.

A buffer solution was prepared using 0.5 g sodium lauryl sulphate, 0.5 g sodium salicylate and 0.25 g disodium edetate dissolved in 10 mL of water. The solution was added to 8 mg (200 units) insulin and mixed, to form micellar insulin.

To this micellar solution were added 0.2 g bacitracin and 0.5 g evening of primrose oil and the solution was mixed vigorously to form a mixed micellar insulin solution (about 20 units/mL).

Six human volunteers were studied. The volunteers fasted from midnight prior to the test, with no food being taken during the 4 hour study.

On the first day, the volunteers received 10 units insulin by injection (regular fast acting insulin, available from Eli Lilly). On the second day, the volunteers received 20 units of the above-prepared oral insulin (twice the injection dose). In both tests, blood glucose levels were monitored at intervals by Bayer's Glucometer Elite.

The results, showing the average for the six volunteers, were as follows:

TABLE XIV

Blood glucose levels (mmol/L)

| Time (minutes) | Oral Dose (20 units) | Injection (10 units) |
|---|---|---|
| 0 | 8.8 | 7.9 |
| 15 | 8.4 | 7.9 |
| 30 | 8.1 | 8.2 |
| 45 | 7.4 | 8.3 |
| 60 | 6.3 | 7.6 |
| 90 | 5.1 | 6.2 |
| 120 | 5.0 | 5.2 |
| 150 | 4.8 | 4.6 |
| 180 | 5.1 | 3.9 |
| 210 | 5.3 | 4.4 |
| 240 | 5.6 | 5.2 |

The results show that the oral insulin formulation of the present invention, at a dosage of twice the injected level, is comparable to the injected insulin.

EXAMPLE 15

A further experiment was performed to show another method of making the mixed micellar formulation of the present invention.

In a 250 mL round bottom flask was added 100 mg of saturated lecithin powder (Phospholipon-90H) purchased from the American Lecithin Co. To this powder was added 5 mL of absolute ethanol (USP grade). The flask was then attached to a rotary evaporator equipped with the vacuum pump and nitrogen inlet for inert atmosphere condition to minimize oxidation of the lecithin. The flask was rotated at 100–150 rpm under vacuum. The solution in the flask was heated to 60° C. by means of water bath to dissolve the powder completely. After complete dissolution of the powder, heating was stopped and the rotation speed was increased to 300 rpm, under vacuum in nitrogen atmosphere until the alcohol evaporated completely, leaving a uniform film on the side of the flask. The rotation was continued for at least 30 minutes to ensure uniform coating of film on the wall and complete solvent removal. After 30 minutes the rotation was stopped and the vacuum was released.

To this flask was added micellar insulin solution which had been prepared from an aqueous solution of insulin, sodium lauryl sulphate, sodium salicylate and disodium edetate. The flask was shaken with the help of shaker plate. Shaking was continued for at least 30 minutes and then the solution was sonicated with a high frequency sonicating probe for another 60 minutes in order to form small uniform mixed micelles. The mixed micelles so obtained were analyzed by Malvern Zeta (trade mark) particle size distribution measurement equipment equipped with the laser light scattering device. The mixed micelles particle size distribution obtained by this method was between 2 and 9 nm. To this solution was added 1 mL of 2% menthol solution and 50 mg sodium hyaluronate. The semi-clear, translucent, light blue colour solution (final volume 10 mL) was stored in a clean glass bottle and refrigerated. The solution had a pH of 6.5.

EXAMPLE 16

Another experiment, within the scope of the present invention, was performed.

A buffer solution was prepared using 0.5 g sodium lauryl sulphate, 0.5 g sodium salicylate and 0.25 g disodium edetate dissolved in 10 mL of water. The solution was added to 8 mg (200 units) insulin and mixed, to form micellar insulin.

To this micellar solution were added 0.5 g borage oil and the solution was mixed vigorously to form a mixed micellar insulin solution (about 20 units/mL).

What is claimed is:

1. A process for making a pharmaceutical composition suitable for delivery through mucosal membranes comprising:

a) preparing a pharmaceutical agent composition in micellar form in an aqueous medium which has an alkali metal salicylate in a concentration of from 1 to 10 wt./wt. % of the aqueous micellar pharmaceutical agent composition, an alkali metal C8 to C22 alkyl sulphate in a concentration of from 1 to 10 wt./wt. % of the aqueous micellar pharmaceutical agent composition and a pharmaceutically acceptable edetate in a concentration of from 1 to 10 wt./wt. % of the aqueous micellar pharmaceutical agent composition;

b) slowly adding the micellar pharmaceutical agent composition, while mixing, to at least one absorption enhancing compound, while continuing to mix vigorously, said absorption enhancing compounds being selected from the group consisting of saturated phospholipid, unsaturated phospholipid, hyaluronic acid, pharmaceutically acceptable salts of hyaluronic acid, octylphenoxypolyethoxyethanol, glycolic acid, lactic acid, chamomile extract, cucumber extract, oleic acid, linolenic acid, borage oil, evening primrose oil, menthol, trihydroxy oxo cholanylglycine and pharmaceutically acceptable salts of trihydroxy oxo cholarylglycine, glycerin, polyglycerin, lysine, polylysine, polidocanol alkyl ethers and analogues of polidocanol alkyl ethers, triolein and mixtures thereof, wherein the amount of each absorption enhancing compound is present in a concentration of from 1 to 10 wt./wt. % of the total formulation, and the total concentration of alkali metal salicylate, alkali metal C8 to C22 alkyl sulphate, edetate and absorption enhancing compounds is less than 50 wt./wt. % of the formulation.

2. A process according to claim 1 wherein there is an additional step of adding, while continuing mixing, at least one absorption enhancing compound different to that added in step b), selected from the group consisting of lecithin, hyaluronic acid, pharmaceutically acceptable salts of hyaluronic acid, octylphenoxypolyethoxyethanol, glycolic acid, lactic acid, chamomile extract, cucumber extract, oleic acid, linolenic acid, borage oil, evening primrose oil, trihydroxy oxo cholanylglycine, glycerin, polyglycerin, lysine, polylysine, triolein and mixtures thereof.

3. A process according to claim 1 wherein the absorption enhancing compound in step b) is selected from the group consisting of lecithin.

4. A process according to claim 1 wherein one of the absorption enhancing compounds is lecithin and another absorption enhancing compound is selected from the group consisting of hyaluronic acid, pharmaceutically acceptable salts of hyaluronic acid and mixtures thereof, the concentration such absorption enhancing compound being from about 1 to about 5 wt./wt. %.

5. A process according to claim 1 wherein the micellar absorption enhancing compounds comprise combinations selected from the group consisting of i) saturated phospholipid and sodium hyaluronate, ii) saturated phospholipid and glycolic acid, iii) lecithin and sodium hyaluronate and iv) saturated phospholipid, glycolic acid and lactic acid.

6. A process according to claim 1 wherein the pharmaceutical agent is selected from the group consisting of insulin, heparin, low molecular weight heparin, hirulog, hirugen, huridine, interferons, interleukins, cytokines, mono and polyclonal antibodies, chemotherapeutic agents, vaccines, glycoproteins, bacterial toxoids, hormones, calcitonins, insulin like growth factors (IGF), glucagon like peptides (GLP-1), large molecule antibiotics, protein based thrombolytic compounds, platelet inhibitors, DNA, RNA, gene therapeutics, antisense oligonucleotides, steroids, hypnotics and pain killers.

7. A process according to claim 1 wherein in step b) the micellar pharmaceutical agent composition is added to lecithin, with sonication, to form a mixed micellar composition; and c) while continuing to mix, adding at least one absorption enhancing compound selected from the group consisting of hyaluronic acid, pharmaceutically acceptable salts of hyaluronic acid, octylphenoxypolyethoxyethanol, glycolic acid, lactic acid, chamomile extract, cucumber extract, oleic acid, linolenic acid, borage oil, evening primrose oil, trihydroxy oxo cholanylglycine, glycerin, polyglycerin, lysine, polylysine, triolein and mixtures thereof;
wherein the amount of lecithin and the absorption enhancing compound are each present in a concentration of from 1 to 10 wt./wt. % of the total formulation, and the total concentration of alkali metal salicylate, alkali metal C8 to C22 alkyl sulphate, edetate and absorption enhancing compounds is less than 50 wt./wt. % of the formulation.

8. A process according to claim 1 wherein the absorption enhancing compound is formed into a film prior to the addition of the micellar pharmaceutical agent composition.

9. A process according claim 1 wherein subsequent to the addition of the micellar pharmaceutical agent composition a second absorption enhancing compound is added, said second absorption enhancing compound being different from the absorption enhancing compound previously used.

10. A process according to claim 1 wherein a phenol selected from the group consisting of phenol, methyl phenol and mixtures thereof is added to the micellar formulation and the resulting formulation placed in a container, and the container is subsequently charged with a propellant.

11. A process according to claim 10 wherein the propellant is selected from the group consisting of tetrafluoroethane, tetrafluoropropane, dimethylfluoropropane, heptafluoropropane, dimethyl ether, n-butane and isobutane.

12. A process according to claim 1 wherein the pharmaceutical agent is insulin.

13. A process according to claim 11 wherein the pharmaceutical agent is insulin.

14. A mixed micellar pharmaceutical formulation comprising a pharmaceutical agent in micellar form, water, an alkali metal C8 to C22 alkyl sulphate in a concentration of from 1 to 10 wt./wt. % of the total formulation, a pharmaceutically acceptable edetate in a concentration of from 1 to 10 wt./wt. % of the total formulation, at least one alkali metal salicylate in a concentration of from 1 to 10 wt./wt. % of the total formulation, and at least one absorption forming compound, said absorption forming compounds being selected from the group consisting of lecithin, hyaluronic acid, pharmaceutically acceptable salts of hyaluronic acid, octylphenoxypolyethoxyethanol, glycolic acid, lactic acid, chamomile extract, cucumber extract, oleic acid, linolenic acid, borage oil, evening primrose oil, menthol, trihydroxy oxo cholanylglycine and pharmaceutically acceptable salts of trihydroxy oxo cholanylglycine, glycerin, polyglycerin, lysine, polylysine, polidocanol alkyl ethers and analogues of polidocanol alkyl ethers, triolein and mixtures thereof, wherein the amount of each absorption enhancing compound is present in a concentration of from 1 to 10 wt./wt. % of the total formulation, and the total concentration of absorption enhancing compounds are less than 50 wt./wt. % of the formulation.

15. A mixed micellar pharmaceutical formulation according to claim 14, in which one of the absorption enhancing compounds is lecithin.

16. A formulation according to claim 14 wherein the alkali metal C8 to C22 alkyl sulphate is sodium lauryl sulphate and the alkali metal salicylate is sodium salicylate.

17. A formulation according to claim 15 wherein the lecithin is selected from the group consisting of sphingomyelin, cephalin, lysolecithin and mixtures thereof.

18. A formulation according to claim 15 wherein the other absorption enhancing compound is selected from the group consisting of hyaluronic acid, pharmaceutically acceptable salts of hyaluronic acid and mixtures thereof, the concentration such absorption enhancing compound being from about 1 to about 5 wt./wt. %.

19. A formulation according to claim 14 wherein the formulation comprises combinations selected from the group consisting of i) sodium lauryl sulphate, sodium salicylate, disodium edetate, saturated phospolipid and sodium hyaluronate; ii) sodium lauryl sulphate, sodium salicylate, disodium edetate, lecithin and sodium hyaluronate; iii) sodium lauryl sulphate, sodium salicylate, disodium edetate, sodium hyaluronate and evening of primrose oil; iv) sodium lauryl sulphate, sodium salicylate, disodium edetate, saturated phospolipid and bacitracin; v) sodium lauryl sulphate, sodium salicylate, disodium edetate, saturated phospolipid, sodium hyaluronate and bacitracin; and vi) sodium lauryl sulphate, sodium salicylate, disodium edetate, sodium hyaluronate, oleic acid and gamma linoleic acid.

20. A formulation according to claim 14 wherein the pharmaceutical agent is selected from the group consisting of insulin, heparin, low molecular weight heparin, hirulog, hirugen, huridine, interferons, interleukins, cytokines, mono and polyclonal antibodies, chemotherapeutic agents, vaccines, glycoproteins, bacterial toxoids, hormones, calcitonins, insulin like growth factors (IGF), glucagon like peptides (GLP-1), large molecule antibiotics, protein based thrombolytic compounds, platelet inhibitors, DNA, RNA, gene therapeutics antisense oligonucleotides, steroids, hypnotics and pain killers.

21. A formulation according to claim 14 wherein the pharmaceutical agent is insulin.

22. A formulation according to claim 21 in which the absorption enhancing compounds are lecithin and a second absorption enhancing compound selected from the group consisting of hyaluronic acid, pharmaceutically acceptable salts of hyaluronic acid and mixtures thereof.

23. A formulation according to claim 14 wherein the formulation additionally comprises a phenol selected from the group consisting of phenol, methyl phenol and mixtures thereof.

24. A formulation according to claim 23 wherein the formulation is contained in an aerosol container and the container is charged with a propellant.

25. A formulation according to claim 24 wherein the propellant is selected from the group consisting of tetrafluoroethane, tetrafluoropropane, dimethylfluoropropane, heptafluoropropane, dimethyl ether, n-butane and isobutane.

26. A process according to claim 6 wherein the pain killer is selected from the group consisting of narcotics and NSAIDs.

27. A formulation according to claim 20 wherein the pain killer is selected from the group consisting of narcotics and NSAIDs.

28. A process according to claim 1 wherein the pharmaceutical agent is an analgesic.

29. A formulation according to claim 14 wherein the pharmaceutical agent is an analgesic.

30. A process according to claim 3 wherein the lecithin is selected from the group consisting of sphingomyelin, cephalin, lysolecithin and mixtures thereof.

* * * * *

UNITED STATES PATENT AND TRADEMARK OFFICE
CERTIFICATE OF CORRECTION

PATENT NO.    : 6,231,882 B1
DATED         : May 15, 2001
INVENTOR(S)   : Pankaj Modi It is certified that error appears in the above-identified patent and that said Letters Patent is hereby corrected as shown below:

Column 3,
Line 2, "90w" should read -- 90% --.

Column 6,
Line 5, place a -- . -- after "enzymes".
Line 6, "of" should read -- Of --.

Column 13,
Line 50, "4.46" should read -- 4.4% --.

Column 21,
Line 6, "cholarylglycine" should read -- cholanylglycine --.

Column 22,
Line 58, delete the words "sphingomyelin, cephalin" and "and mixtures thereof."
Claim 17 should read -- 17. A formulation according to claim 15 wherein the lecithin is selected from the group consisting of lysolecithin. --

Signed and Sealed this

Third Day of June, 2003

JAMES E. ROGAN
*Director of the United States Patent and Trademark Office*